United States Patent
Kostansek (12)

(10) Patent No.: US 6,426,319 B1
(45) Date of Patent: Jul. 30, 2002

(54) DELIVERY SYSTEMS FOR CYCLOPROPENES REQUIRING LESS WATER

(75) Inventor: Edward Charles Kostansek, Buckingham, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/957,752

(22) Filed: Sep. 21, 2001

Related U.S. Application Data

(60) Provisional application No. 60/236,659, filed on Sep. 29, 2000.

(51) Int. Cl.[7] .................. A01N 25/10; A01N 25/28; A01N 27/00
(52) U.S. Cl. ..................... 504/357; 504/359
(58) Field of Search ................. 504/357, 359

(56) References Cited

U.S. PATENT DOCUMENTS 5,518,998 A    5/1996  Bäckström et al. ............ 514/3
6,017,849 A  * 1/2000  Daly et al. .................. 504/114

* cited by examiner

*Primary Examiner*—S. Mark Clardy
(74) *Attorney, Agent, or Firm*—Thomas D. Rogerson

(57) ABSTRACT

The present invention relates to new delivery systems for cyclopropenes in which compositions comprising the cyclopropene and a molecular encapsulation agent complex further comprise additional components which provide slow release of the cyclopropene from the molecular encapsulating agent with water, or release of the cyclopropene from the molecular encapsulating agent with only small amounts of water, or both. The present invention also provides methods to release a cyclopropene from such compositions as well as methods to deliver a cyclopropene compound to a plant to inhibit an ethylene response in the plant.

10 Claims, No Drawings

DELIVERY SYSTEMS FOR CYCLOPROPENES REQUIRING LESS WATER

CROSS REFERENCE TO RELATED PATENT APPLICATIONS

This is a non-provisional application of prior pending U.S. provisional application Ser. No. 60/236,659 filed Sep. 29, 2000.

The present invention relates to new delivery systems for cyclopropenes in which compositions comprising the cyclopropene and a molecular encapsulation agent complex comprise additional components which provide enhanced release of the cyclopropene from the molecular encapsulating agent using water. Such cyclopropenes and their derivatives, such as methylcyclopropene, are capable of inhibiting the ethylene response in plants. The cyclopropene/molecular encapsulating agent complexes provide a convenient means for storing and transporting the cyclopropenes which are reactive gases and highly unstable because of oxidation and other potential reactions. Such complexes also provide convenient methods of delivering these compounds to plants in order to extend the plant's shelf life.

It is well known that ethylene can cause the premature death of plants or plant parts including, for example, flowers, leaves, fruits, and vegetables through binding with certain receptors in the plant. Ethylene also promotes leaf yellowing and stunted growth as well as premature fruit, flower, and leaf drop. Because of these ethylene-induced problems, very active and intense research presently concerns the investigation of ways to prevent or reduce the deleterious effects of ethylene on plants. U.S. Pat. No. 5,518,988 discloses the use of cyclopropene and its derivatives, including methylcyclopropene, as effective blocking agents for ethylene binding. However, a major problem with these compounds is that they are typically unstable gases which present explosive hazards when compressed. As a solution to these problems, U.S. Pat. No. 6,017,849 discloses a method of incorporating these gaseous compounds into a molecular encapsulation agent complex in order to stabilize their reactivity and thereby provide a convenient and safe means of storing, transporting and applying or delivering the active compounds to plants. For the most active cyclopropene derivative disclosed in U.S. Pat. No. 5,518,988, 1-methylcyclopropene, the preferred molecular encapsulation agent is a cyclodextrin, with α-cyclodextrin being the most preferred. The application or delivery of these active compounds to plants is accomplished by simply adding water to the molecular encapsulation agent complex. The complex is prepared according to the methods disclosed in U.S. Pat. No. 6,017,849 which provides the material in the form of a powder.

The 1-methylcyclopropene/α-cyclodextrin complex noted above releases the 1-methylcyclopropene very quickly. However, in order to accomplish this release large amounts of water are required, at least ten times and preferably twenty times the weight of the 1-methylcyclopropene/α-cyclodextrin complex. It would be advantageous to accomplish complete release of the cyclopropene from the complex using a minimal amount of water. This would allow a user to treat flowers, fruits, or vegetables with the cyclopropene gas directly in shipping containers, rather than a large treatment container, chamber, or room.

We have surprisingly found that small amounts of absorbed water are sufficient to release 1-methylcyclopropene from the 1-methylcyclopropene/α-cyclodextrin complex. In one embodiment of the present invention powdered complex is mixed with a water absorbent material such as a powdered superabsorbent polymer. Such polymers include, for example, sodium polyacrylate. The mixture is then placed in a sachet which can be made from a variety of materials including, as one example, filter paper. When this sachet is dipped in water for 10 seconds and then placed in a container, it slowly releases the 1-methylcyclopropene gas. In another embodiment of the invention, a deliquescent compound is mixed with the powdered complex and placed in a sachet. When this sachet is placed in a humid environment, such as an environment typical for the storage of flowers, fruits, and vegetables, the 1-methylcyclopropene gas again is slowly released. Although the delivery systems of this invention provide slow release of 1-methylcyclopropene they still provide complete release. This same process is equally applicable to other cyclopropene/molecular encapsulation agent complexes.

The present invention is, therefore, a composition comprising:

a) a molecular encapsulation agent within which a cyclopropene of the formula:

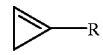

wherein R
is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;
is encapsulated;

b) optionally one or more adjuvants; and c) a water absorbent material.

As used herein, the term "alkyl" means both straight and branched chain ($C_1$–$C_{20}$) radicals which include, for example, methyl, ethyl, n-propyl, isopropyl, 1-ethylpropyl, n-butyl, tert-butyl, isobutyl, 2,2-dimethylpropyl, pentyl, octyl, and decyl. The terms "alkenyl" and "alkynyl" mean ($C_3$–$C_{20}$)alkenyl and ($C_3$–$C_{20}$)alkynyl groups such as, for example, 2-propenyl, 2-butenyl, 3-butenyl, 2-methyl-2-propenyl, and 2-propynyl. The term "cycloalkylalkyl" means a ($C_1$–$C_{15}$) alkyl group substituted with a ($C_3$–$C_6$) cycloalkyl group such as, for example cyclopropylmethyl, cyclopropylethyl, cyclobutylmethyl, and cyclopentylethyl. The term "haloalkyl" means an alkyl radical wherein one or more of the hydrogen atoms have been replaced by a halogen atom. The term "halogen" means fluorine, chlorine, bromine, and iodine.

Preferably, R is ($C_1$–$C_{10}$) alkyl. More preferably, R is ($C_1$–$C_8$) alkyl. Even more preferably R is ($C_1$–$C_4$) alkyl. Most preferably, R is methyl.

Preferred encapsulating agents include cyclodextrins, crown ethers, polyoxyalkylenes, polysiloxanes, and zeolites. More preferred encapsulating agents include α-cyclodextrin, β-cyclodextrin, and γ-cyclodextrin. The most preferred encapsulating agent, particularly when the cyclopropene is 1-methylcyclopropene, is alpha-cyclodextrin. The most preferred encapsulating agent will vary depending upon the size of the R substituent. However, as one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

The cyclopropenes applicable to this invention are known materials prepared using the processes disclosed in U.S. Pat. Nos. 5,518,988 and 6,017,849. The cyclopropene/molecular encapsulation agent complexes of the present invention are prepared by contacting the cyclopropene with a solution or slurry of the molecular encapsulation agent and then isolating the complex, again using general processes disclosed in U.S. Pat. No. 6,017,849. In the case of 1-methylcyclopropene, the gas is bubbled through a solution of α-cyclodextrin in water from which the complex first precipitates and is then isolated by filtration.

It is often desirable to include in the composition one or more adjuvants, such as extenders, binders, lubricants, surfactants and/or dispersants, wetting agents, spreading agents, dispersing agents, stickers, adhesives, defoamers, thickeners, emulsifying agents and the like. Such adjuvants commonly used in the art can be found in the John W. McCutcheon, Inc. publication *Detergents and Emulsifiers, Annual*, Allured Publishing Company, Ridgewood, N.J., U.S.A.

A wide variety of water absorbent materials may be used in the compositions of this invention. These include one or more organic materials such as superabsorbent polymers, such as, for example, sodium polyacrylate (crosslinked), polysaccharides, acrylamide/acrylate copolymers, and carboxymethylcellulose; one or more inorganic deliquescent compounds such as, for example, calcium chloride, magnesium chloride, lithium chloride, zinc chloride, magnesium nitrate, and aluminum nitrate; and combinations and mixtures thereof.

The combinations described above can be placed in sachets of various compositions or included in multilayer film systems. A typical sachet resembles a tea bag in form and/or construction and would be stored in a water impermeable container until just prior to use. Alternatively, the composition itself may be placed in a water impermeable container until just prior to use. Such containers include, for example, vials, sealed foil pouches, sealed plastic or polymer pouches, polymer microspheres, multilayer films, and monolithic polymer structures. In another embodiment of this invention, the water absorbent material is prepared as a gel which is kept separated from the complex by various physical means until release is desired. The gel and complex are then mixed to release the cyclopropene. Physical means to keep the materials separated include, for example, multichamber vials, multichamber pouches, and multilayer thick films.

The compositions of this invention may comprise from 3 percent to 97 percent, by weight, cyclopropene/encapsulation agent complex and 3 percent to 97 percent, by weight, water absorbent material. Preferably, the compositions of this invention comprise:

| | |
|---|---|
| 1-methylcyclopropene/α-cyclodextrin complex | 5–95% |
| Water absorbent polymer | 5–95% |
| or | |
| 1-methylcyclopropene/α-cyclodextrin complex | 3–90% |
| Deliquescent compound | 10–97% |

More preferably, the compositions of this invention comprise:

| | |
|---|---|
| 1-methylcyclopropene/α-cyclodextrin complex | 15–50% |
| Water absorbent polymer | 50–85% |
| or | |
| 1-methylcyclopropene/α-cyclodextrin complex | 10–30% |
| Deliquescent compound | 70–90% |

Even more preferably, the compositions of this invention comprise:

| | |
|---|---|
| 1-methylcyclopropene/α-cyclodextrin complex | 20–30% |
| Water absorbent polymer | 70–80% |
| or | |
| 1-methylcyclopropene/α-cyclodextrin complex | 10–20% |
| Deliquescent compound | 80–90% |

Most preferably, the compositions of this invention comprise:

| | |
|---|---|
| 1-methylcyclopropene/α-cyclodextrin complex | 25% |
| Water absorbent polymer | 75% |
| or | |
| 1-methylcyclopropene/α-cyclodextrin complex | 15% |
| Deliquescent compound | 85% |

These ratios will change for different cyclopropenes, different encapsulation agents, and water absorbent material due to differences in molecular weights, cyclopropene uptake by the encapsulation agents, and water absorbing ability of the water absorbent compound. One skilled in the art can easily determine the optimum ratios for these various combinations.

Another embodiment of this invention is a method to release a cyclopropene from the composition of this invention, comprising the step of contacting the composition with water. Such contact may, for example, range from dipping a sachet containing the complex into water to exposing the complex to a humid environment as described above.

Another embodiment of this invention is a method to deliver a cyclopropene compound to a plant to inhibit an ethylene response in the plant comprising the step of contacting the composition of this invention with water in the presence of the plant.

Some embodiments of this invention are illustrated by the following examples.

EXAMPLE 1

1-Methylcyclopropene Release by Humidity

A dry-blend mixture of 50% 1-methylcyclopropene ("MCP")α-cyclodextrin complex powder and 50% dextrose powder (by weight) was prepared as a control and as a starting material for blending with various additives. Two samples were prepared. The first involved blending 0.1 g of the mixture with 0.5 g calcium chloride powder and placing this mixture in a high humidity chamber, being careful not to allow the powder blend to contact any water directly. The second involved blending 0.1 g of the mixture with 3.0 g calcium chloride powder and placing this mixture in a high humidity chamber, again being careful not to allow the powder blend to contact any water directly. Two concurrent controls were run using the mixture alone first control was treated in the same manner as the calcium chloride blends described above except that 0.10 g of the dry-blend mixture was used without the calcium chloride. The second control used 0.10 g of the dry-blend mixture directly dissolved in 2 ml of a 15% calcium chloride solution. The 1-methylcyclopropene release characteristics of the samples were determined by periodically analyzing the headspace of each for 1-methylclopropene. The analysis method used gas chromatography with a flame ionization detector. Table 1 shows the resulting release profiles of the four sample systems.

TABLE 1

| Release Time (hours) | 0 g CaCl$_2$ % MCP Released (Control) | 0.5 g CaCl$_2$ % MCP Released | 3 g CaCl$_2$ % MCP Released | CaCl$_2$ soln % MCP Released (Control) |
|---|---|---|---|---|
| 0.5 | 0.7 | 8 | 1 | 90 |
| 1.1 | 1.6 | 21 | 1.5 | 100 |
| 2 | 3.6 | 41 | 2 | |
| 3 | 5.7 | 53 | 5 | |
| 4 | | 62 | 9 | |
| 5 | 7.2 | 69 | 12 | |
| 7 | | 84 | 22 | |
| 9 | | 88 | 29 | |
| 24 | | 93 | 51 | |

The results clearly show that 1-MCP can be released from the dry-blend mixture plus calcium chloride just by the water provided by humidity. Release is slower than from the powder dissolved directly in the liquid. However, this is often an advantage when treating small containers. When no deliquescent salt is present, the 1-methylcyclopropene does release, but it is very slow and takes several days to reach the same level of release achieved by the 0.5 g calcium chloride system in only 9 hours.

EXAMPLE 2

1-Methylcyclopropene Release by Limited Exposure to Water

A dry-blend mixture of 50% 1-methylcyclopropene/α-cyclodextrin complex powder and 50% dextrose powder (by weight) was prepared as a control and as a starting material for blending with the superabsorbent polymers ASAP® 1100 (Chemdal Corp-BASF, Portsmouth, Va.) and Sanwet® IM-300 (Sanyo Chemical, Kyoto, Japan). Samples were prepared by mixing 0.3 g of the dry-blend mixture with 1.0 g polymer powder and placing the blend in a filter paper sachet. The sachet was then dipped in water for 10 seconds and placed in a chamber which was then sealed. The 1-methylcyclopropene release characteristics of the delivery systems were determined by periodically analyzing the headspace of each for 1-methylcyclopropene as in Example 1. The dry-blend mixture alone, as a control, was placed in a sachet, dipped in water, and analyzed in the same manner. Table 2 shows the resulting average release profiles produced from the two superabsorbent polymer samples and the control.

TABLE 2

| Release Time (hours) | ASAP® % MCP Released | Sanwet® % MCP Released | Control® % MCP Released |
|---|---|---|---|
| 0 | 18 | 5 | 44 |
| 0.12 | 57 | | 81 |
| 0.23 | 71 | | 88 |

TABLE 2-continued

| Release Time (hours) | ASAP® % MCP Released | Sanwet® % MCP Released | Control® % MCP Released |
|---|---|---|---|
| 0.35 | 79 | | 94 |
| 0.47 | 85 | | 100 |
| 0.58 | 85 | | |
| 1 | 85 | 47 | |
| 2 | 100 | 67 | |
| 18 | | 93 | |

The 1-Methylcyclopropene release profiles demonstrate that the sachets dipped in water release the active ingredient well and at a slower rate than the dry-blend mixture alone.

EXAMPLE 3

1-Methylcyclopropene with Slower Release by Limited Exposure to Water

This example is a repeat of Example 2 with ASAP® 1100 superabsorbent polymer except that the dry-blend mixture was enclosed in a polyvinylalcohol pouch before adding it to the sachet containing the superabsorbent polymer. Table 3 shows the release characteristics of this system. The pouch significantly delays the wetting of the dry-blend mixture and demonstrates a delayed (24 hr.) 1-methylcyclopropene release rather than the 2 hr. 1-methylcyclopropene release profile for material in the absence of the polyvinylalcohol pouch.

TABLE 3

| Release Time (hrs) | ASAP® (% MCP Released) | PVA/ASAP® (% MCP Released) |
|---|---|---|
| 0 | 18 | 0 |
| 0.5 | 79 | 16 |
| 1 | 85 | 22 |
| 2 | 100 | 28 |
| 16 | | 69 |
| 24 | | 77 |

I claim:
1. A composition comprising:
   a) a molecular encapsulation agent within which a cyclopropene of the formula:

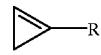

wherein R
   is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;
   is encapsulated;
   b) optionally one or more adjuvants; and
   c) a water absorbent material.
2. The composition of claim 1, wherein R is $(C_1-C_8)$alkyl.
3. The composition of claim 1, wherein R is methyl.
4. The composition of claim 1, wherein the molecular encapsulation agent is a cyclodextrin or a mixture of cyclodextrins.
5. The composition of claim 1, wherein the molecular encapsulation agent is α-cyclodextrin.

6. The composition of claim 1, wherein the water absorbent material is:
   a) one or more polymers; or
   b) one or more deliquescent compounds; or
   c) a mixture thereof.

7. The composition of claim 1, wherein the water absorbent material is a superabsorbent polymer.

8. A article of manufacture comprising the composition of claim 1 enclosed in a water impermeable container.

9. A method to release a cyclopropene from the composition of claim 1, comprising the step of contacting the composition with water.

10. A method to deliver a cyclopropene compound to a plant to inhibit an ethylene response in the plant, comprising the step of contacting the composition of claim 1 with water in the presence of the plant.

* * * * *